United States Patent
Nobutoki et al.

[11] Patent Number: 6,086,794
[45] Date of Patent: Jul. 11, 2000

[54] ORGANIC NONLINEAR OPTICAL MATERIAL AND NONLINEAR OPTICAL ELEMENT USING THE SAME

[75] Inventors: Hideharu Nobutoki; Tetsuyuki Kurata, both of Tokyo, Japan

[73] Assignee: Mitsubishi Denki Kabushiki Kaisha, Tokyo, Japan

[21] Appl. No.: 09/012,577

[22] Filed: Jan. 23, 1998

[30] Foreign Application Priority Data

Mar. 26, 1997 [JP] Japan ................................ 9-073160

[51] Int. Cl.$^7$ ................ F21V 9/00; G02B 6/00; G02F 1/35
[52] U.S. Cl. .................... 252/582; 252/587; 385/122; 385/143; 359/328; 359/329; 549/59; 558/54
[58] Field of Search ........................ 252/582, 587; 385/122, 143; 359/329, 328; 549/59; 558/54

[56] References Cited

U.S. PATENT DOCUMENTS

| | | | |
|---|---|---|---|
| 4,087,554 | 5/1978 | Haydock et al. | 424/353 |
| 4,607,116 | 8/1986 | Yamazaki et al. | 560/21 |
| 4,659,840 | 4/1987 | Shimizu et al. | 548/549 |
| 5,286,901 | 2/1994 | Stang et al. | |

OTHER PUBLICATIONS

Tsugio Kitamura et al., Synthesis, pp. 945–946, "A Convenient Preparation of Diaryliodonium Triflates", Oct. 1992.

Tsugio Kitamura, et al., Bulletin of the Chemical Society of Japan, vol. 68, No. 12, pp. 3637 to 3641, Alkenyl– and Alkynyl–Substituted (p–Phenylene)Bisiodonium Ditriflates by Reactions of a (p–Phenylene)Bisiodine(III) Reagent with Alkynes and 1–Trimethylsilyl–1–Alkynes, 1995.

Peter J. Stang, et al., Tetrahedron Letters, vol. 33, No. 11, pp. 1419 to 1422, "(Dicyano)Iodonium Triflate—Novel Iodonium Species and a Versatile Reagent for the Preparation of Iodonium Salts via an Iodonium Transfer Reaction with Organostannanes", 1992.

Tsugio Kitamura, et al., Tetrahedron Letters, vol. 34, No. 25, pp. 4055 to 4058, "Novel Cyclization to Benzofurans in the Reaction of Alkylnyl(p–Phenylene)Bisiodonium Ditriflates with Phenoxide Anion", 1993.

Peter J. Stang., Journal of the American Chemical Society, vol. 113, No. 12, pp. 4571 to 4576, "Preparation and Chemistry of PhI$^+$C=CI$^{30}$ Ph.2$^-$OTf, Bis(Phenyl[[(Trifluoromethyl)Sulfonyl]Iodo]Acetylene, A Novel Difunctional Acetylene, Bis(Iodonium) Species and a Stable C$_2$–Transfer Agent", 1991.

Rik R. Tykwinski, et al., Journal of Organic Chemistry, vol. 58, No. 19, pp. 5235 to 5237, "A New Synthesis of Alkynyl Sulfones and Single Crystal X–Ray Structure of P–(Tolysulfonyl)Ethyne", 1993.

(List continued on next page.)

*Primary Examiner*—Philip Tucker
*Attorney, Agent, or Firm*—Oblon, Spivak, McClelland, Maier & Neustadt, P.C.

[57] ABSTRACT

An organic nonlinear optical material comprising a compound having the iodonium salt structure represented by the general formula (I):

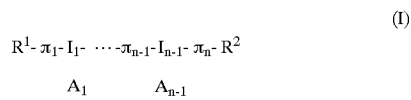

(I)

wherein $\pi_1$ to $\pi_n$ are the same or different and each is an atomic group having $\pi$ electron, $I_1$ to $I_{n-1}$ are an iodonium cation, $A_1$ to $A_{n-1}$ are the same or different and each is a counter anion for the iodonium cation, $R^1$ and $R^2$ are the same or different and each is a hydrogen atom or an electron donative group, and n is an integer of 2 to 4. The material has large nonlinear optical constants and shows no light absorption in the visible light region.

8 Claims, 7 Drawing Sheets

OTHER PUBLICATIONS

Rik R. Tykwinski, et al., Tetrahedron, vol. 49, No. 15, pp. 3043 to 3051, "Functionalization of Diynes. Preparation of Bis(Alkynyl) Ditosylate and Dibenzoate Esters and Bis-(Alkynyl) Dithiocyanates via Alkynyl Iodonium Chemistry", 1993.

Tsugio Kitamura, et al., "Preparation of (p–Phenylene) bis (aryliodonium) Ditriflates and Their Double Substitution by Some Nucleophiles," Journal of Organic Chemistry, vol. 57, No. 25, (1992), pp. 6810–6814.

Paul M. Gallop, et al., "Highly Effective PQQ Inhibition by Alkynyl and Aryl Mono– and Diiodonium Salts," Journal of Amercian Chemical Society, vol. 115, No. 25, (1993), pp. 11702–11704.

Carl W. Dirk, et al., "Squarylium Dyes: Structural Factors Pertaining to the Negative Third–Order Nonlinear Optical Response," Journal of American Chemical Society, vol. 117, No. 8, (1995), pp. 2214–2225.

FIG. 2
LUMO
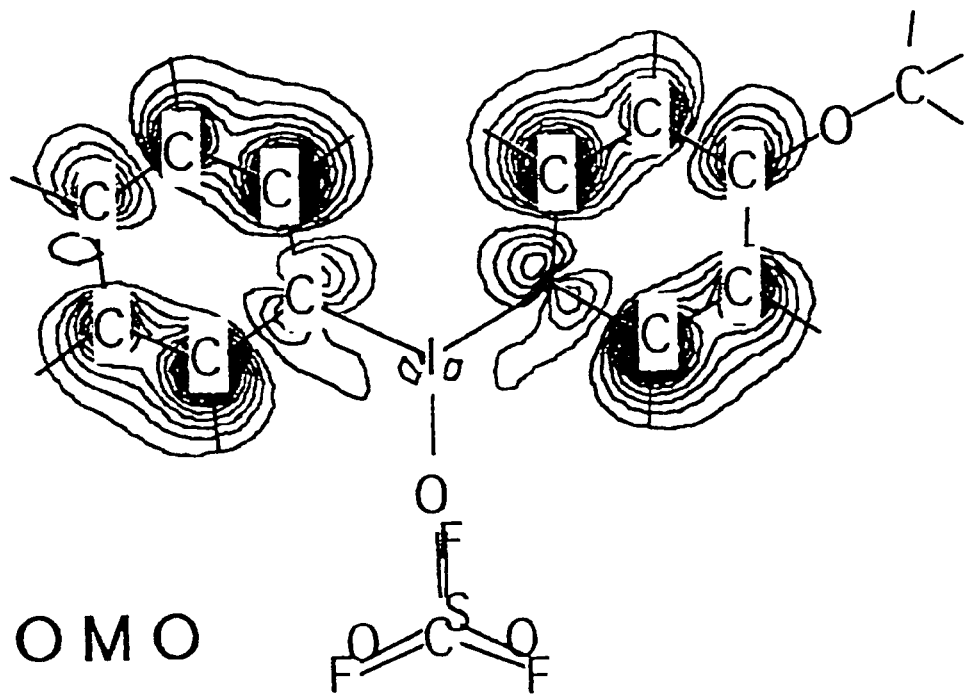
HOMO
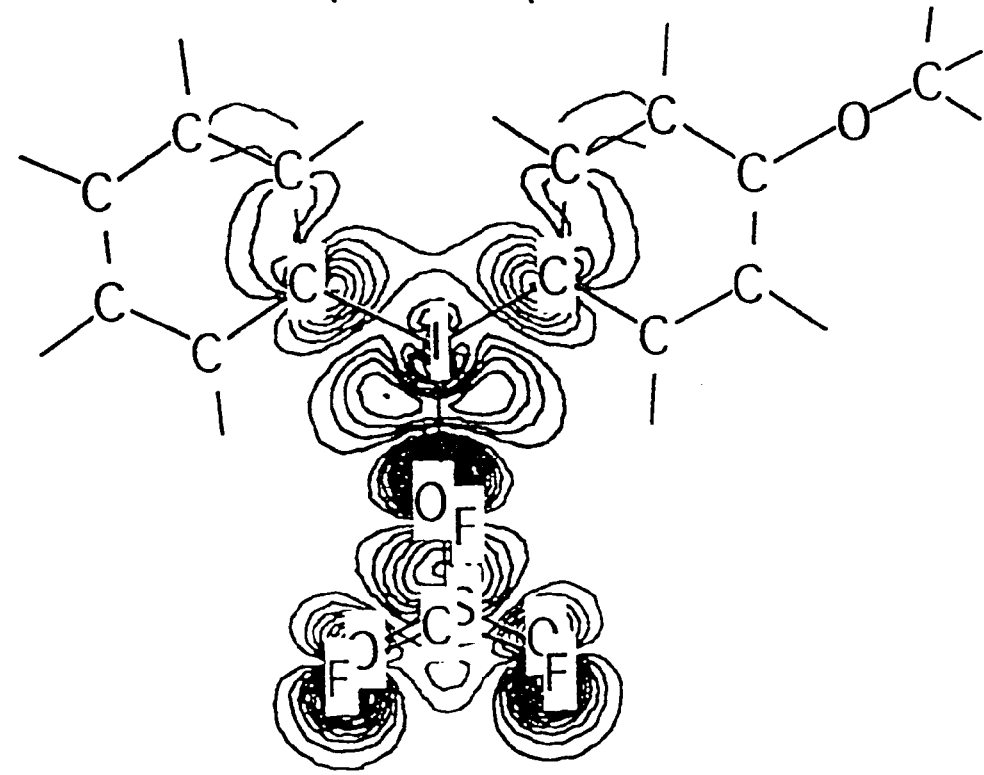

ORGANIC NONLINEAR OPTICAL MATERIAL AND NONLINEAR OPTICAL ELEMENT USING THE SAME

BACKGROUND OF THE INVENTION

The present invention relates to an organic nonlinear optical material. Such a material can be utilized as a material for nonlinear optical elements, such as waveguides and the like, which constitute optically functional devices, such as electrooptical devices, all optical devices and the like, for use in optical communication, optical computer and the like.

Since nonlinear optical materials are those showing second-order or third-order nonlinear optical response in electric field of light and have functions such as amplification, oscillation, wavelength conversion, refractive index conversion and the like, they are said to be a fundamental material for optical communication, optical computer and the like. Inter alia, nonlinear optical materials showing third-order nonlinear optical response display nonlinear refractive index effect and optical bistability, and hence, they are expected to be applied to high-speed optical switch, optical logical element, optical memory and the like.

However, the conventional organic nonlinear optical materials are excellent in high-speed responsiveness as compared with inorganic materials but have small third-order nonlinear optical properties. As a result, they have been hardly applied to the aforementioned devices. For example, organic nonlinear optical materials described in Hachiro Nakanishi and Shuji Okada, "Third-order Nonlinear Optical Materials and Their Applications", O plus E, 1996, No. 4, pages 68–74 have small third-order nonlinear optical constant $\chi^{(3)}$ of $10^{-10}$ to $10^{-12}$ esu as obtained by third harmonic generation measurement and have not been applied to electrooptical devices, all optical devices and the like for use in optical communication, optical computer and the like. In addition, since the aforementioned $\chi^3$ values are those obtained by utilizing the resonance state of molecules, there is a problem on the thermal stability of the materials. Thus, it is difficult to permanently use the organic nonlinear optical material in the above-mentioned elements. Further, since the conventional organic nonlinear optical materials exhibit a great light absorption in the visible region, the application of the materials to the aforementioned elements is unsuitable due to their large light transmission loss.

As described above, there is a problem that since the conventional organic nonlinear optical materials have small nonlinear optical constants, such nonlinear optical constants are those obtained by utilizing the resonance state of molecules and the materials themselves exhibit a great light absorption in the visible region, they have not been applied to electrooptical devices, all optical devices and the like for use in optical communication, optical computer and the like.

In view of the foregoing, it is an object of the present invention to provide an organic nonlinear optical material which has nonlinear optical properties superior to those of the conventional organic nonlinear optical materials and which can be applied to electrooptical devices, all optical devices and the like for use in optical communication, optical computer and the like.

Another object of the present invention to provide a nonlinear optical element using the organic nonlinear optical material.

Still another object of the present invention to provide a nonlinear optical device using the nonlinear optical element.

SUMMARY OF THE INVENTION

The present invention provides organic nonlinear optical materials and a nonlinear optical element as follows:

(1) An organic nonlinear optical material comprising a compound having the iodonium salt structure represented by the general formula (I):

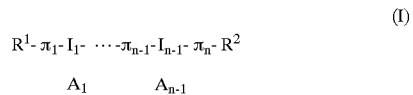

wherein $\pi_1$ to $\pi_n$ are the same or different and each is an atomic group having $\pi$ electron, $I_1$ to $I_{n-1}$ are an iodonium cation, $A_1$ to $A_{n-1}$ are the same or different and each is a counter anion for the iodonium cation, $R^1$ and $R^2$ are the same or different and each is a hydrogen atom or an electron donative group, and n is an integer of 2 to 4.

(2) The organic nonlinear optical material set forth in (1), wherein $\pi_1$ to $\pi_n$ are the same or different and each is an atomic group selected from the group consisting of benzene, biphenyl, thiophene, acetylene, ethynylbenzene, diethynylbenzene, vinylbenzene, naphthalene and anthracene.

(3) The organic nonlinear optical material set forth in (1) or (2), wherein $R^1$ and $R^2$ are the same or different and each is a member selected from the group consisting of hydrogen atom, alkoxy group, hydroxyl group, amino group, dialkylamino group, alkyl group and trialkylsilyl group.

(4) The organic nonlinear optical material set forth in (2) or (3), wherein in the general formula (I), n=2, $\pi_1=\pi_2=$ benzene ring, $A_1=$trifluoromethanesulfonate ion, $R^1=$H and $R^2=$methoxy group.

(5) The organic nonlinear optical material set forth in (2) or (3), wherein in the general formula (I), n=3, $\pi_1=\pi_2=\pi_3=$ benzene ring, $A_1=A_2=$trifluoromethanesulfonate ion, $R^1=$H and $R^2=$methoxy group.

(6) The organic nonlinear optical material set forth in (2) or (3), wherein in the general formula (I), n=2, $\pi_1=\pi_2=$ biphenyl ring, $A_1=$trifluoromethanesulfonate ion, $R^1=$H, and $R^2=$methoxy group.

(7) The organic nonlinear optical material set forth in (2) or (3), wherein in the general formual (I), n=3, $\pi_1=\pi_3=$ benzene ring, $\pi_2=$thiophene ring, $A_1=A_2=$ trifluoromethanesulfonate ion, and $R^1=R^2=$H.

(8) The organic nonlinear optical material set forth in (2) or (3), wherein in the general formula (I), n=3, $\pi_1=\pi_3=$ thiophene ring, $\pi_2=$benzene ring, $A_1=A_2=$ trifluoromethanesulfonate ion, and $R^1=R^2=$H.

(9) The organic nonlinear optical material set forth in (2) or (3), wherein in the general formula (I), n=3, $\pi_1=\pi_2=$ benzene ring, $\pi_3=$phenyleneethynylene group, $A_1=A_2=$ trifluoromethanesulfonate ion, and $R^1=R^2=$H.

(10) The organic nonlinear optical material set forth in (2) or (3), wherein in the general formula (I), n=3, $\pi_1=\pi_2=$ benzene ring, $\pi_3=$ethynylene group, $A_1=A_2=$ trifluoromethanesulfonate ion, and $R^1=$H, and $R^2=$t-butyl group.

(11) An organic nonlinear optical material comprising at least one compound represented by the general formula (I), set forth in any one of (1) to (10), wherein the compound is dissolved or dispersed in a low-molecular compound, a high-molecular compound or a liquid medium.

(12) A nonlinear optical element usable as a light transmitting medium having a nonlinear refractive index or a nonlinear absorption coefficient in combination with an optical element in a nonlinear optical device, the nonlinear optical element comprising an organic nonlinear optical material set forth in any one of (1) to (11).

(13) A nonlinear optical device of a waveguide structure comprising a light transmitting medium as a waveguide in combination with an optical element, the light transmitting medium comprising a nonlinear optical element set forth in (12).

(14) The device set forth in (13), which is capable of performing a switching operation by application of a modulated electric field.

(15) The device set forth in (13), wherein the light transmitting medium has a bulk type structure.

(16) The device set forth in (13), wherein the light transmitting medium has an optical fiber structure.

BRIEF DESCRIPTION OF THE DRAWINGS

FIG. 2 is a diagram showing highest occupied molecular orbital (HOMO) and lowest unoccupied molecular orbital (LUMO) obtained with respect to Compound No. 1 used in Example 1.

DETAILED DESCRIPTION

Figure 1:
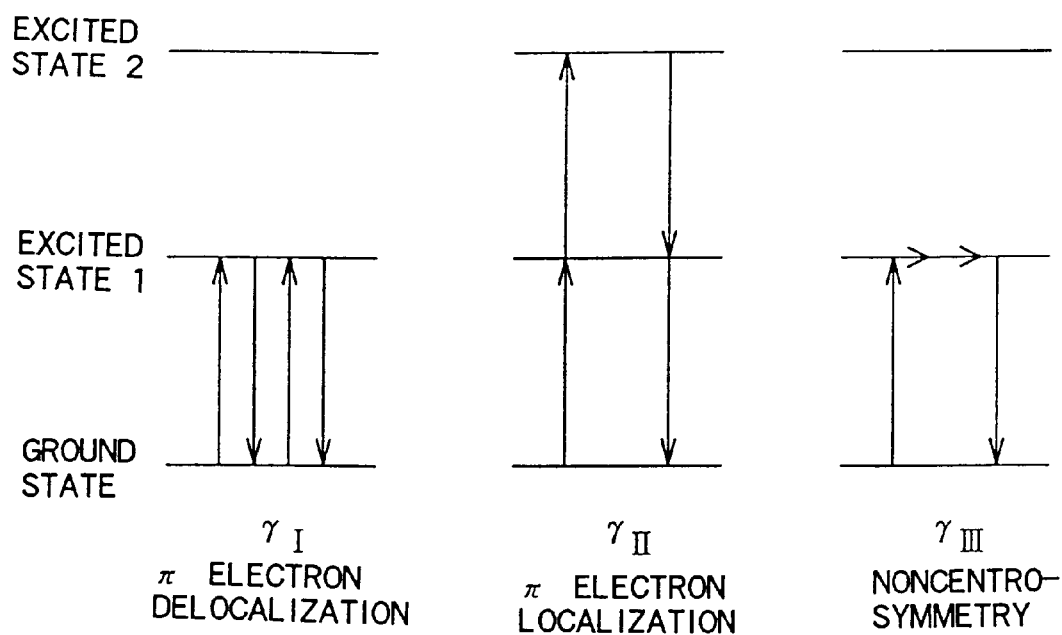
FIG. 1 is a schematic view showing three transition processes contributing to second-order hyperpolarizability γ of a molecule.

The present invention will be described in detail.

The organic nonlinear optical material of the present invention comprises a compound having the iodonium salt structure represented by the general formula (I):

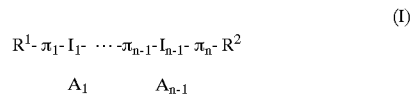

wherein $\pi_1$ to $\pi_n$ are the same or different and each is an atomic group having π electron, $I_1$ to $I_{n-1}$ are an iodonium cation, $A_1$ to $A_{n-1}$ are the same or different and each is a counter anion for the iodonium cation, $R^1$ and $R^2$ are the same or different and each is a hydrogen atom or an electron donative group, and n is an integer of 2 to 4.

The compounds represented by the aforementioned general formula (I) include the following three types depending upon the number of n.

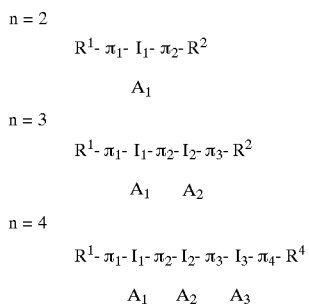

The atomic group having π electron represented by $\pi_1$ to $\pi_n$, which constitutes the organic nonlinear optical material of the present invention is not limited to specified one as long as it complies with the aforementioned definition. Examples thereof include ethylene, acetylene, benzene, vinylbenzene, ethynylbenzene, diethynylbenzene, biphenyl, naphthalene, anthracene, aniline, carbazole, thiophene, furan, pyrrole, imidazole, selenophene, pyridine, quinoline, pyrazine, quinoxaline, purine, and derivatives thereof. Although all these compounds can be used, those that constitute π-conjugated system throughout the entire molecule are desirable from the viewpoint of nonlinear optical properties and optical responsibility. In view of this, one or a combination of two or more selected from the group consisting of benzene, biphenyl, thiophene, acetylene, ethynylbenzene, diethynylbenzene, vinylbenzene, naphthalene and anthracene is preferable.

These compounds are each present as a bivalent atomic group in the molecule of the compound represented by the general formula (I). However, the compound which is bonded to $R^1$ or $R^2$ is monovalent atomic group when $R^1$ or $R^2$ is H.

In addition, the counter anion represented by $A_1$ to $A_{n-1}$ which constitutes the organic nonlinear optical material of the present invention is not limited to specified one as long as it complies with the aforementioned definition. Examples thereof include anions such as trifluoromethanesulfonate, tetrafluoroborate, hexafluorophosphate, hexafluoroantimonate, methanesulfonate, p-toluenesulfonate, and derivatives thereof. Although all these anions can be used, those having great anionic properties are desirable from the viewpoint of the stability of the iodonium salt structure. In view of this, anions such as trifluoromethanesulfonate, hexafluoroantimonate, methanesulfonate and p-toluenesulfonate are particularly preferable.

Further, the electron donative group represented by $R^1$ and $R^2$ which constitutes the organic nonlinear optical material of the present invention is not limited to specified one as long as it complies with the aforementioned definition. Examples thereof include alkoxy groups having 1 to 3 carbon atoms such as methoxy group, ethoxy group and propoxy group, hydroxy group, amino group, dialkylamino groups wherein amino group is substituted with alkyl group having 1 to 3 carbon atoms such as dimethylamino group, diethylamino group and dipropylamino group, alkyl groups having 1 to 6 carbon atoms such as methyl group, ethyl group, propyl group, n-butyl group, t-butyl group and hexyl group, trialkylsilyl groups wherein silyl group is substituted with alkyl group having 1 to 3 carbon atoms such as trimethylsilyl group, triethylsilyl group and tripropylsilyl group, and derivatives thereof. Although all these groups can be used, groups having great electron donative property are desirable from the viewpoint of nonlinear optical properties and optical responsibility and the stability of the iodonium salt structure. In view of this, methoxy group, ethoxy group, t-butyl group, hydroxyl group, amino group, dimethylamino group, diethylamino group and trimethylsilyl group are particularly preferable.

With reference to the drawings, it will be described that the aforementioned organic nonlinear optical material shows high nonlinear optical properties.

Using three-level model, second-order hyperpolarizability γ of molecule can be described by the following equation:

$$\gamma \approx \gamma_I + \gamma_{II} + \gamma_{III} \quad (II)$$

wherein $\gamma_I$, $\gamma_{II}$ and $\gamma_{III}$ are as follows:

$$\gamma_I \propto -\mu_{01}^4 D_{11} \quad (III)$$

$$\gamma_{II} \propto \mu_{01}^2 \mu_{12}^2 D_{121}$$

$$\gamma_{III} \propto \mu_{01}^2 (\mu_{11} - \mu_{00})^2 D_{111}$$

wherein $\mu_{01}$ is transition dipole moment to one-photon state, and $\mu_{12}$ is transition dipole moment between one-photon state and two-photon state. $D_{1m}$ and $D_{1mn}$ are energy dispersion terms.

FIG. 1 schematically shows transition process in $\gamma_I$, $\gamma_{II}$ and $\gamma_{III}$. Herein, $\gamma_I$, $\gamma_{II}$ and $\gamma_{III}$ are transition process resulting from π electron delocalization, transition process resulting from π electron localization and transition process resulting from noncentrosymmetrical structure, respectively. As shown in FIG. 1, one-photon state (low energy) participates in $\gamma_I$ and $\gamma_{III}$ but two-photon state (high energy) participates in $\gamma_{II}$. Since localization of π electron in manifestation of nonlinear optical effect has a problem on optical responsibility, π electron is required to be delocalized. Therefore, transition process $\gamma_{II}$ if resulting from localization of π electron is not useful. Transition process contributing to γ is $\gamma_I$ and $\gamma_{III}$ and both are transition process in two-level system.

Then, the aforementioned equation (II) can be approximately treated as two-level model, where γ can be expressed by the following equation.

$$\gamma \alpha (-\mu_{ge}^4/\omega_{ge}^3) + \mu_{ge}^2 [(\mu_{ee} - \mu_{gg})^2/\omega_{ge}^3)] \quad (IV)$$

wherein $\mu_{ge}$ is transition dipole moment between ground (g) state and excited (e) state, $\mu_{gg}$ and $\mu_{ee}$ indicate dipole moments in ground state and excited state, respectively, and $\omega_{ge}$ indicates energy gap between both states. Regarding molecules having centrosymmetry, the aforementioned equation (IV) is expressed as follows:

$$\gamma \alpha f_{ge}(L_{ee} - L_{gg}) \quad (V)$$

where $f_{gg}$ is oscillator strength between ground state and excited state, and $L_{gg}$ and $L_{ee}$ indicate extension of electrons in ground state and excited state, respectively.

From the aforementioned equations (IV) and (V), in order to render γ larger, it is required that difference between charge distribution in ground state and that in excited state be large, overlap between electron clouds in ground state and excited state be large, and energy gap between ground state and excited state be large. Here, small energy gap between ground state and excited state has a problem because light transmittance is deteriorated. Therefore, it is important that π electron is delocalized, difference between charge distribution in ground state and that in excited state is large and overlap of electron clouds between both states is large. This is imparted by the structure which has a backbone of a π electron conjugated system as a fundamental skeleton and modifies the electronic state of the π electron conjucated system of the backbone itself. Here, an example of the structure which modifies the electronic state of π electron conjugated backbone itself is a self-doped structure which conjugates with π electron. The iodonium salt structure in the present invention is a self-doped structure and, since it has dπ electron, it can also conjugates with π electron. Since the iodonium salt structure in the present invention has delocalized π electron, large difference between charge distribution in ground state and that in excited state, and large overlap of electron clouds between both states, it can manifest large γ.

The compound represented by the aforementioned general formula (I) can be used as an organic nonlinear optical material as it is. Alternatively, the compound can be used as an organic nonlinear optical material in a state wherein it is dissolved or dispersed in a low-molecular compound or a high-molecular compound (including prepolymer). Examples of the low-molecular compounds are biphenyl, terphenyl, anthracene, chrysene, benzophen, benzophenone, benzil, pyrene, perylene and carbazole. These low-molecular compounds may be used either alone or in combination of two or more species thereof. Examples of the high-molecular compounds are poly(meth)acrylates such as polymethyl methacrylate, polymers obtained by thermal or photo polymerization of prepolymers described below. These high-molecular compounds may be used either alone or in combination of two or more species thereof. Examples of the prepolymers are ethylene glycol di(meth)acrylate, diethylene glycol di(meth)acrylate, triethylene glycol di(meth)acrylate, tetraethylene glycol di(meth)acrylate, polyethylene glycol di(meth)acrylate, propylene glycol di(meth)acrylate, dipropylene glycol di(meth)acrylate, tripropylene glycol di(meth)acrylate, polypropylene glycol di(meth)acrylate, butanediol di(meth)acrylate, hexamethylene glycol di(meth)acrylate, bis[(meth)acryloxyethyl] phthalate, bis[(meth)acryloxypropyl]phthalate, bis[(meth)acryloxyethyl]isophthalate, bis[(meth)acryloxypropyl] isophthalate, bis[(meth)acryloxyethyl]terephthalate, bis[(meth)acryloxypropyl]terephthalate, bis[(meth)acryloxyethoxyphenyl]propane, bis[(meth)acryloxydiethoxyphenyl]propane, bis[(meth)acryloxypropoxyphenyl]propane, bis[(meth)acryloxydipropoxyphenyl]propane, bisphenol A di(meth)acrylate, hydrogenated bisphenol A di(meth)acrylate, trimethylolmethane-tri(meth)acrylate, trimethylolethane-tri (meth)acrylate, trimethylolpropane-tri(meth)acrylate, tetramethylolmethane-tri(meth)acrylate, tetramethylolethane-tri(meth)acrylate, tetramethylolpropane-tri(meth)acrylate, tetramethylolmethane-tetra(meth)acrylate, tetramethylolethane-tetra(meth)acrylate, and tetramethylolpropane-tetra( meth) acrylate. These prepolymers may be used either alone or in combination of two or more species thereof. When these prepolymers are used, they are cured with radical polymerization initiator, ultraviolet ray or the like.

Alternatively, the compound represented by the aforementioned general formula (I) can be used in a state where it is dissolved or dispersed in a liquid medium. Examples of the liquid media are tetrahydrofuran, dichloromethane, trichloromethane, carbon tetrachloride, dichloroethane, dimethylsulfoxide, and chlorobenzene. These liquid media may be used either alone or in combination of two or more species thereof.

The organic nonlinear optical material of the present invention can be applied to nonlinear optical elements as a light transmitting medium or the like for use in waveguide-type or bulk-type all optical switching devices, high-speed optical modulator and the like by utilizing properties such as nonlinear refractive index and nonlinear absorption coefficient thereof. Such nonlinear optical elements may be prepared by appropriate methods such as vacuum deposition method, molecular beam deposition method, molecular beam epitaxial growth method, cluster ion beam method, pulse laser method, spin coating method, dipping method, LB method and roll coating method. The shape of the nonlinear optical element of the present invention is not particularly limited. Examples of the shapes include a film, a sheet, a plate, a rod, a fiber, and a bulk crystal.

The present invention will be described by way of Examples but are not limited thereto.

EXAMPLE 1

As an example of the organic nonlinear optical material of the present invention, there is shown a compound wherein n=2, $\pi_1$=phenyl group, $\pi_2$=p-phenylene group, $A_1$=trifluoromethanesulfonate ion, $R^1$=H and $R^2$=methoxy group in the general formula (I), i.e., the compound (Compound No. 1) represented by the following formula:

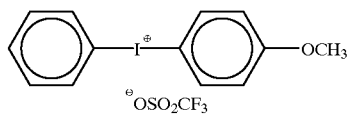

The method for preparing Compound No. 1 is not limited to specified one. For example, Compound No. 1 can be prepared by a chemical synthetic method described in detail in J. Org. Chem., Vol. 57, No. 25, pages 6810–6814 (1992), J. Am. Chem. Soc., Vol. 115, No. 25, pages 11702–11704 (1993), and Bulletin of Society of Organic Synthesis Chemistry, Vol. 53, No. 10, pages 69–81 (1995).

By non-empirical molecular orbital calculation, the electron state of Compound No. 1 was obtained. FIG. 2 three-dimensionally shows highest occupied molecular orbital (HOMO) corresponding to ground state of the compound and lowest unoccupied molecular orbital (LUMO) corresponding to excited state, which were obtained by the calculation. In HOMO, π electron is greatly delocalized on the iodine atom, the carbon atom on the benzene ring adjacent to the iodine atom, and the sulfonyl group. On the other hand, in LUMO, π electron is greatly delocalized on the benzene ring. Further, as seen from FIG. 2, difference between charge distribution in HOMO and that in LUMO is large, and overlap between electron clouds of both orbitals is large on the carbon atom on the benzene ring adjacent to the iodine atom. That is, it was found that this compound has delocalized π electron, large difference between charge distribution in ground state and that in excited state, and large overlap between electron clouds in both states. This means that the compound has the structure which has π electron conjugated backbone as a fundamental skeleton and modulates electronic state of π electron conjugated backbone itself.

Figure 3:
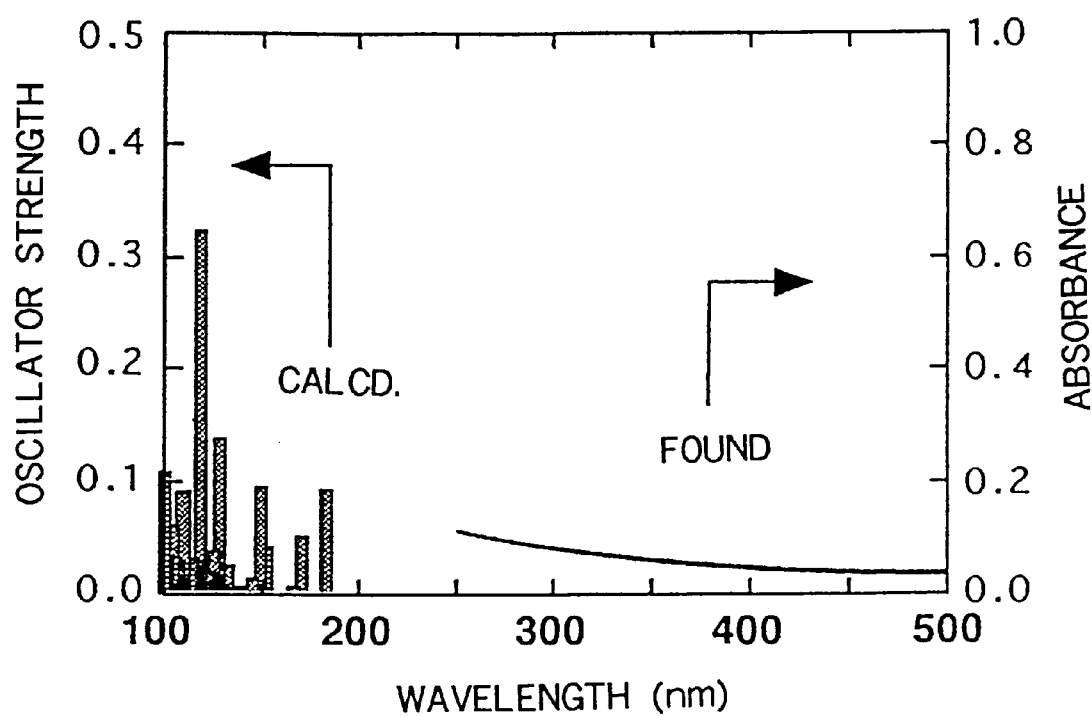
FIG. 3 is ultraviolet and visible absorption spectra (measured and calculated) of Compound No. 1 used in Example 1.

FIG. 3 shows ultraviolet and visible absorption spectra of Compound No. 1 obtained by semi-empirical molecular orbital calculation and experiment. This compound was found to show light absorption in visible light region and be excellent in light transmittance.

From the electron state obtained by the aforementioned calculation, γ value in electrostatic field, i.e., γ (0;0,0,0) value was obtained by using CPHF (dependent coupled perturbed Hartree-Fock) method, which was found to be γ (0;0,0,0)=13×10$^{-34}$ esu.

In addition, Compound No. 1 was deposited on a fused silica substrate by a vacuum deposition method to prepare a deposited film. The $\chi^{(3)}$ value of this deposited film was obtained by THG (third harmonic generation)-Maker-fringe method, i.e., by measuring THG of the fused silica having the known $\chi^{(3)}$ value at the same time and determining $\chi^{(3)}$ value from a ratio of THG of the fused silica and that of the sample. At a foundamental wave of 1.06 μm, $\chi^{(3)}$ value~10$^{-12}$ esu was obtained. That is, it was found that although this compound has high light transmittance in visible light region, it shows great nonlinear optical constants.

EXAMPLE 2

As an example of the organic nonlinear optical material of the present invention, there is shown a compound wherein n=3, $\pi_1$=phenyl group, $\pi_2$=$\pi_3$=p-phenylene group, $A_1$=$A_2$=trifluoromethanesulfonate ion, $R^1$=H and $R^2$=methoxy group in the general formula (I), i.e., the compound (Compound No. 2) represented by the following formula:

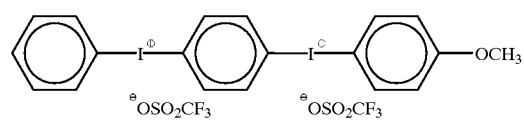

According to the same calculation method as in Example 1, the γ (0;0,0,0) value of this compound was obtained, which was found to be γ (0;0,0,0)=13×10$^{-34}$ esu.

In addition, this compound was prepared in the same manner as in Example 1 and the $\chi^{(3)}$ value was obtained by using the same THG-Maker-fringe method, which was found to be $\chi^{(3)}$ value~10$^{-12}$ esu at a fundamental wave of 1.06 μm.

EXAMPLES 3–23

Using compounds (Compound Nos. 3–23) shown in Tables 1–3, the same calculation method as in Example 1 was employed to obtain γ (0;0,0,0) value, and it was found that all compounds gave large γ (0;0,0,0) values.

TABLE 1
| Ex. No. | Compound No. | Structural formula | γ (0; 0, 0, 0) (× $10^{-34}$ esu) |
|---|---|---|---|
| 3 | 3 | 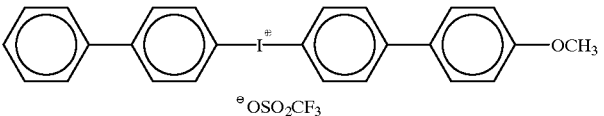 | −25 |
| 4 | 4 | 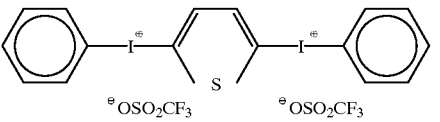 | −667 |
| 5 | 5 | 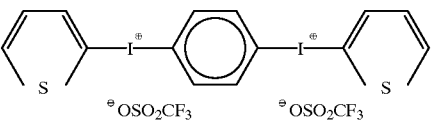 | 319 |
| 6 | 6 | 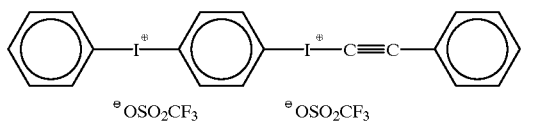 | 134 |
| 7 | 7 | 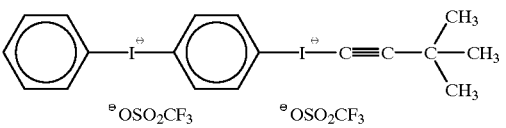 | 108 |
| 8 | 8 | 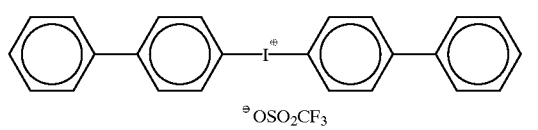 | −46 |
| 9 | 9 | 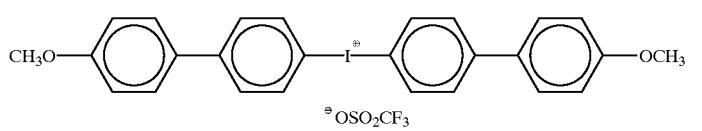 | −26 |
TABLE 2
| Ex. No. | Compound No. | Structural formula | γ (0; 0, 0, 0) (× $10^{-34}$ esu) |
|---|---|---|---|
| 10 | 10 | 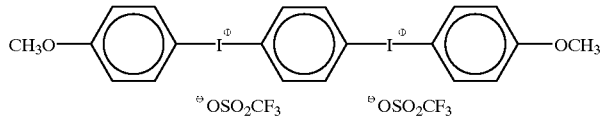 | 68 |
| 11 | 11 | 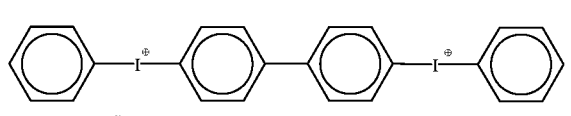 | 124 |

TABLE 2-continued

| Ex. No. | Compound No. | Structural formula | $\gamma$ (0; 0, 0, 0) ($\times 10^{-34}$ esu) |
|---|---|---|---|
| 12 | 12 | Ph—I⁺—C₆H₄—C₆H₄—I⁺—C₆H₄—OCH₃, 2 ⁻OSO₂CF₃ | 124 |
| 13 | 13 | CH₃O—C₆H₄—I⁺—C₆H₄—C₆H₄—I⁺—C₆H₄—OCH₃, 2 ⁻OSO₂CF₃ | 75 |
| 14 | 14 | Ph—I⁺—C≡C—I⁺—Ph, 2 ⁻OSO₂CF₃ | 15 |
| 15 | 15 | Ph—I⁺—C≡C—C₆H₄—C≡C—I⁺—Ph, 2 ⁻OSO₂CF₃ | 31 |
| 16 | 16 | Ph—I⁺—C₆H₄—I⁺—C≡C—n-C₄H₉, 2 ⁻OSO₂CF₃ | 61 |

TABLE 3

| Ex. No. | Compound No. | Structural formula | $\gamma$ (0; 0, 0, 0) ($\times 10^{-34}$ esu) |
|---|---|---|---|
| 17 | 17 | Ph—I⁺—C₆H₄—I⁺—C≡C—n-C₆H₁₃, 2 ⁻OSO₂CF₃ | 76 |
| 18 | 18 | Ph—I⁺—C₆H₄—I⁺—C≡C—Si(CH₃)₃, 2 ⁻OSO₂CF₃ | 55 |
| 19 | 19 | Ph—I⁺—C₆H₄—C₆H₅, ⁻OSO₂CF₃ | −24 |
| 20 | 20 | (2-thienyl)—I⁺—(2-thienyl), ⁻OSO₂CF₃ | −87 |

TABLE 3-continued

| Ex. No. | Compound No. | Structural formula | γ (0; 0, 0, 0) (× 10⁻³⁴ esu) |
|---|---|---|---|
| 21 | 21 | [structure with two C≡C–I⁺–phenyl groups on benzene, two ⁻OSO₂CF₃ counterions] | −149 |
| 22 | 22 | [structure with thiophene–I⁺–CH=CH–thiophene–CH=CH–OCH₃, ⁻OSO₂CF₃ counterion] | −237 |
| 23 | 23 | [structure: phenyl–I⁺–phenyl–I⁺–phenyl–I⁺–phenyl, three ⁻OSO₂CF₃ counterions] | 842 |

EXAMPLES 24–25

Compound No. 1 was added to a solution polymethyl methacrylate (PMMA) in tetrahydrofuran and mixed uniformly, and the solvent was distilled off to give an organic nonlinear optical material containing Compound No. 1 at 0.005 mol/liter (Example 24). An organic nonlinear optical material containing Compound No. 2 at 0.001 mol/liter was obtained in the same manner as above (Example 25). The same THG-Maker-fringe method as in Example 1 was used to obtain $\chi^{(3)}$ value, which was found to be $\chi^{(3)}$ value~$10^{-12}$ esu at a fundamental wave of 1.06 μm for both materials.

EXAMPLE 26

Figure 4:
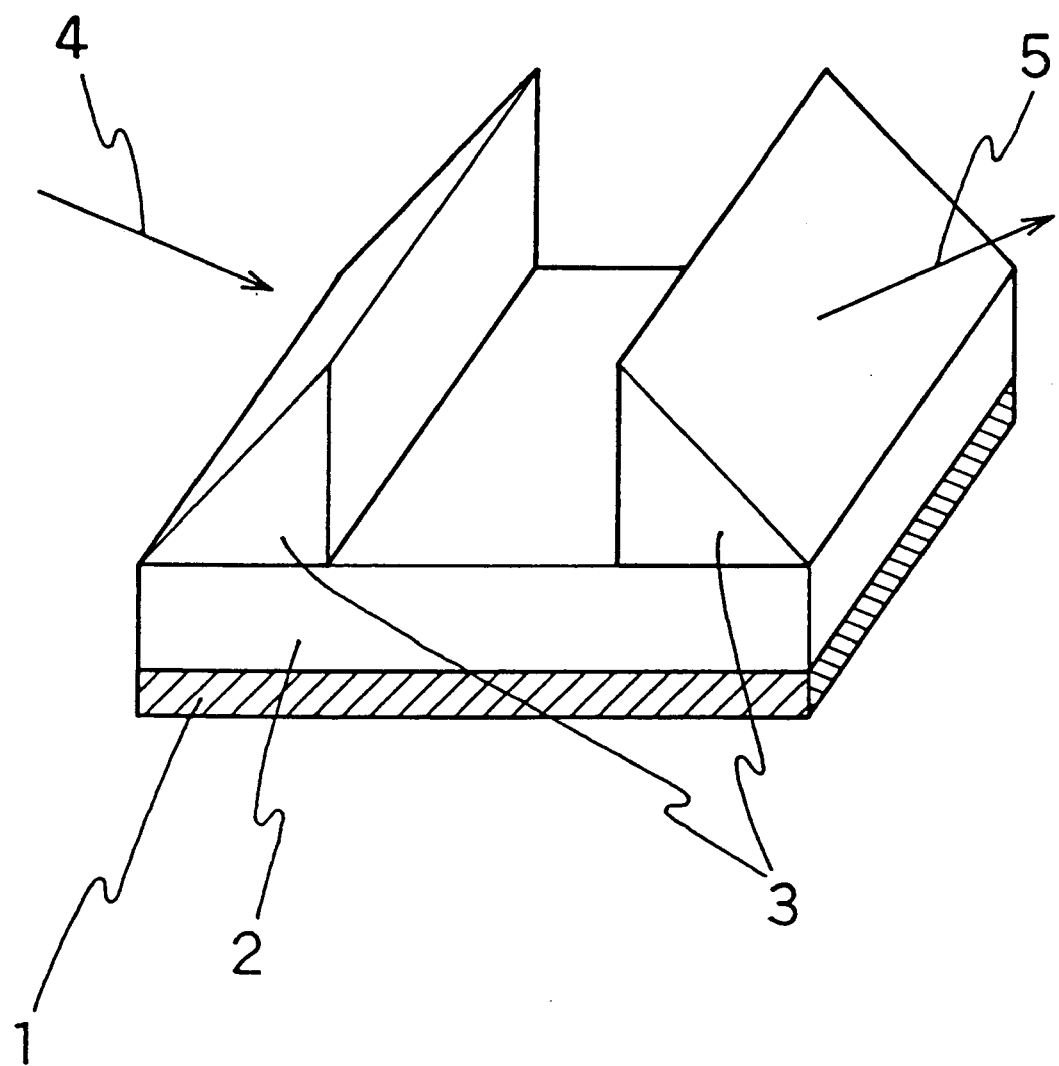
FIG. 4 is a schematic view showing the structure of a slab type waveguide according to the present invention.

Compound No. 1 was deposited on a silica glass substrate of 20 mm×10 mm×1 mm at a thickness of 2,000 nm by a vacuum deposition method. A waveguide of slub type as shown in FIG. 4 was fabricated using the substrate. In FIG. 4, 1 denotes a waveguide layer composed of the organic nonlinear optical material of the present invention (deposited film of Compound No. 1), 2 denotes the silica glass substrate, 3 denotes prisms, 4 denotes incident light, and 5 denotes output light.

Figure 5:
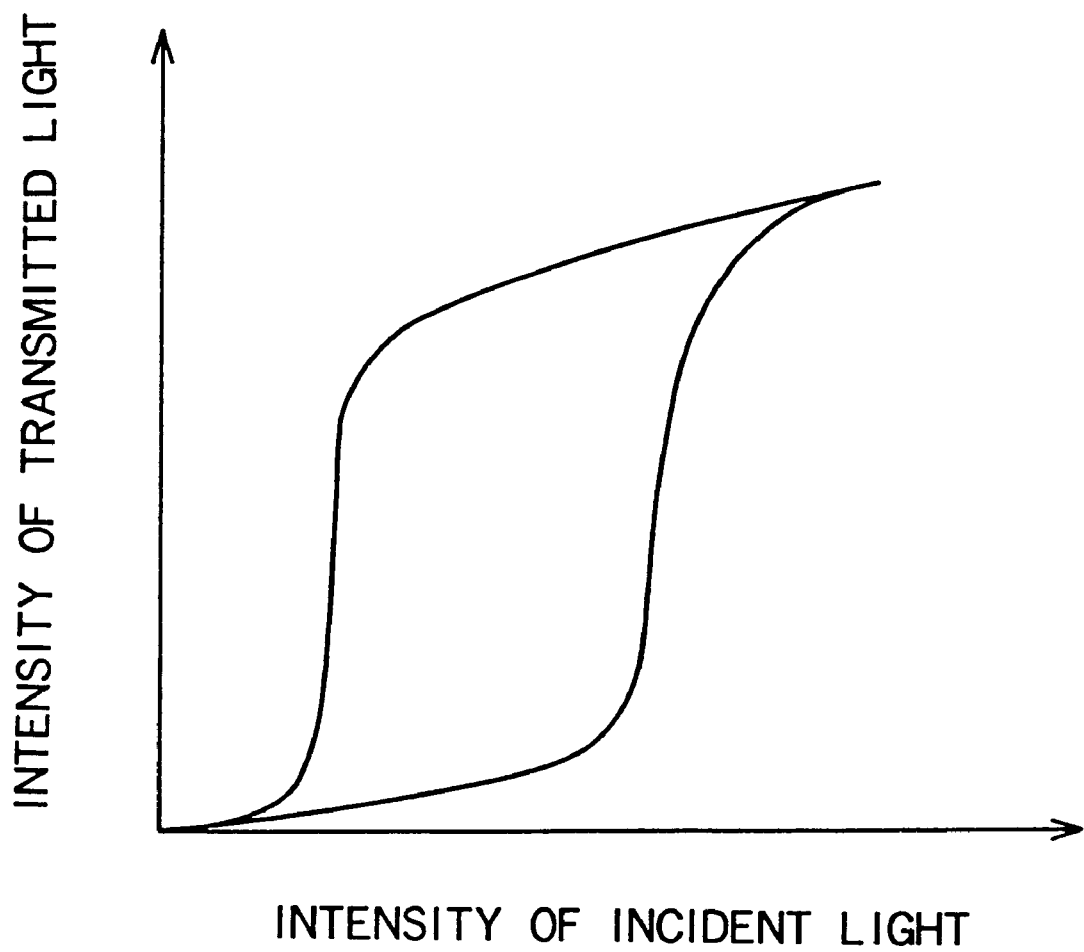
FIG. 5 is a graph showing the properties of optical bistable device of Example 26.

Continuous-wave laser light of a wavelength of 830 nm obtained by combining an argon ion laser and a dye laser was allowed to be incident on one prism in the device and the transmitted light which was the light outputted from the other prism was detected with a high-speed photodiode. The incident light was high-speed-modulated at frequency of 1 GHz with a high-speed light modulator, a part of which was taken out as trigger. The trigger from the incident light and the output from the transmitted light were inputted to X-Y of an oscilloscope to plot Lissajous's figure, which demonstrates achievement of bistability as shown in FIG. 5. In that case, operation power was in the order of mW and optical bistable device having high-speed responsibility at low threshold was obtained.

In the above-mentioned Example 26, a waveguide of slab type was used. However, a waveguide of channel type can also be used. The means of coupling with input light and output light may be either prism coupling or end-fiber coupling.

EXAMPLE 27

Figure 6:
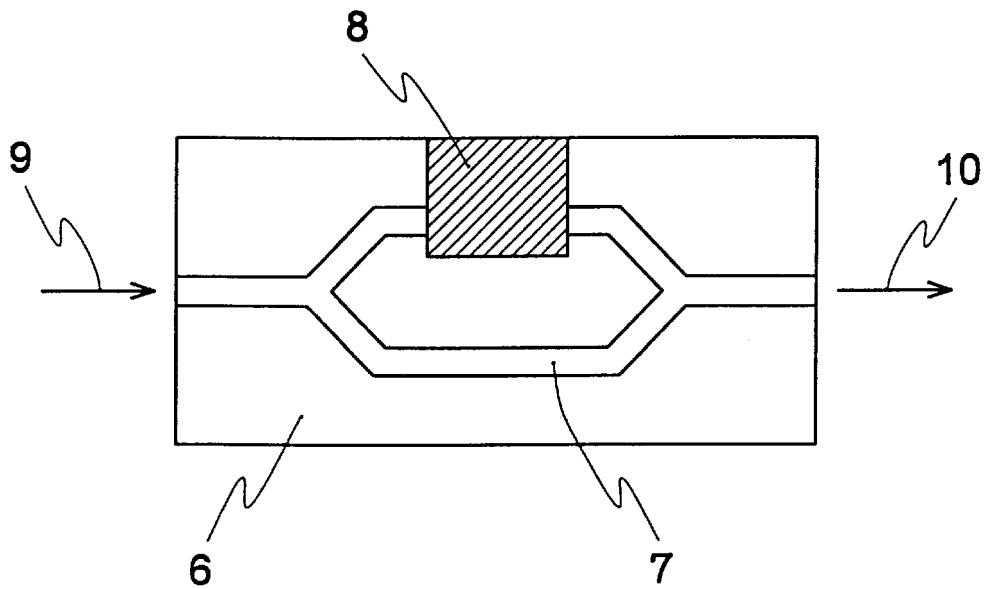
FIG. 6 is a schematic view showing the structure of an optical switching device with Mach-Zehnder type waveguide according to the present invention.

An optical switching device with Mach-Zehnder type waveguide channel using the organic nonlinear optical material of the present invention as shown in FIG. 6 was fabricated. In FIG. 6, 6 denotes a substrate (clad), 7 denotes a waveguide channel (core), 8 denotes a film of the organic nonlinear optical material of the present invention. 9 and 10 denote incident light and output light, respectively.

Gerumanium oxide was doped into a silica glass substrate 6 of 10 mm×10 mm×1 mm by use of a conventional lithography to form a pattern of Mach-Zehnder waveguide channel 7 wherein the difference in refractive index between the waveguide channel 7 and the substrate was 0.3. The waveguide channel 7 had a size of 8 μm×8 μm in its section and the angle between the two branched channels was two degrees. The film 8 was formed by depositing the compound described in Example 2 (Compound No. 2) onto the one of the branched channels 7 in an optical pass length of 3 mm by a vacuum deposition method.

Helium-neon laser light of a wavelength of 633 nm was allowed to be incident as the input light 9 and the output light 10 was detected with a high-speed photodiode. The refractive index of the film 8 of the organic nonlinear optical material varied depending upon the intensity of the input light 9 due to the third-order nonlinear optical effect, thereby causing changes in phase difference between the light beams passing the two branched channels. The intensity of the output light 10 showed a sigmoid change due to interference between the two light beams, which demonstrated that the device of this example acted as an optical switching device with Mach-Zehnder type waveguide channel.

EXAMPLE 28

Figure 7:
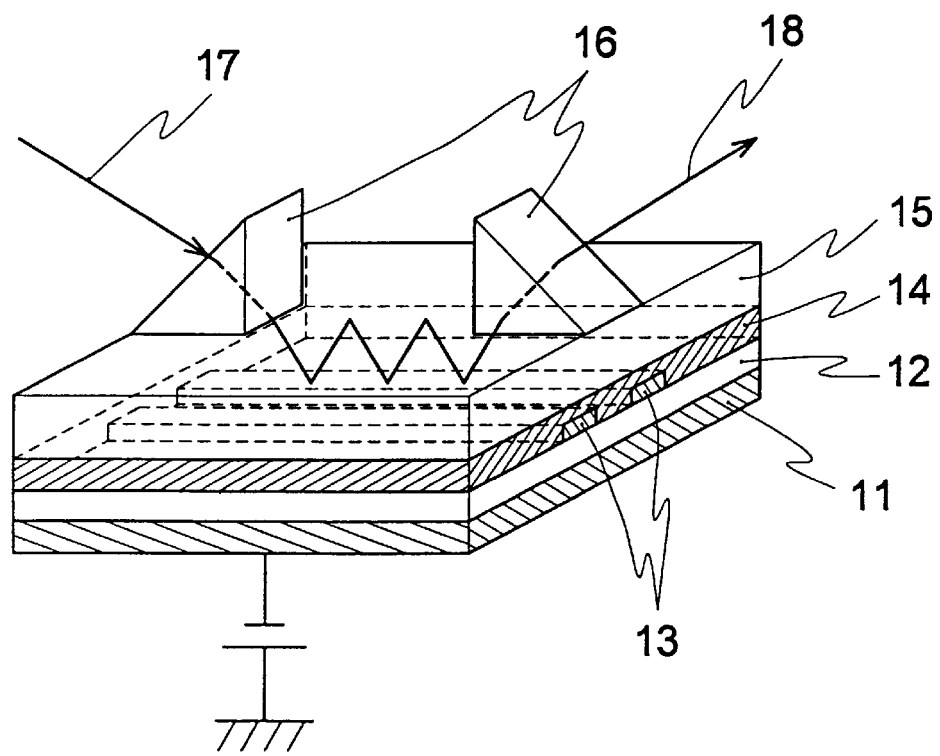
FIG. 7 is a schematic view showing the structure of an optical switching device with field modulation type waveguide according to the present invention.

An optical switching device with field modulation type waveguide channel using the organic nonlinear optical material of the present invention as shown in FIG. 7 was fabricated. In FIG. 7, 11 denotes an electrode (gate) for applying a modulated electric field, 12 denotes an insulating layer, 13 denotes source/drain electrodes, 14 denotes a film of the organic nonlinear optical material of the present invention, 15 denotes an overcoat layer, 16 denotes prisms. 17 and 18 denote input light and output light, respectively.

A highly doped silicon substrate was used as the electrode 11 for applying a modulated electric field. The insulating layer 12 was made of silicon oxide. The source/drain electrodes were made of gold and chromium, respectively. The width and length of a channel defined by the source/drain electrodes 13 were 0.8 mm and 10 mm, respectively. The film 14 was formed by depositing the compound described in Example 2 (Compound No. 2) to a thickness of 100 nm onto the insulating layer 12 by a vacuum deposition method. The overcoat layer was formed by using Cytop (made by Asahi Glass Co., Ltd., refractive index: 1.34). The overcoat layer 15 and the film 14 function as a core for the waveguide channel and the guided light is transmitted between a pair of electrodes 13. The transmittance of the guided light is controlled by applying a gate voltage through the electrode 11, thereby switching the output light 18.

Helium-neon layser light of a wavelength of 633 nm was allowed to be incident as the input light 17 and a modulated voltage of 100 V was applied, providing a modulation factor of 20% within the range between DC and 10 Hz. Thus, an optical switching operation due to modulation of light intensity was confirmed.

EXAMPLE 29

Figure 8:
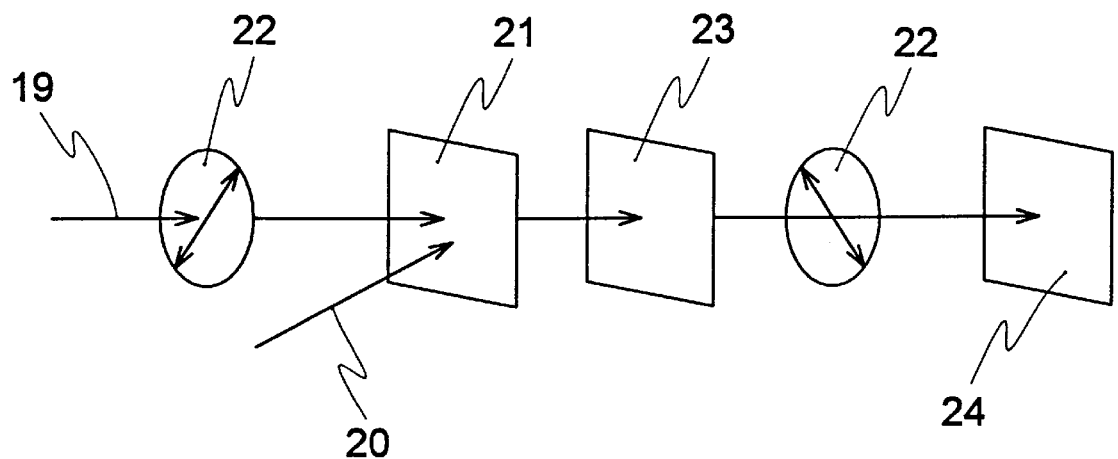
FIG. 8 is a schematic view showing the arrangement of a bulk type optical Kerr shutter device according to the present invention.

The compound described in Example 2 (Compound No. 2) was used to form a thick membrane having a thickness of 5 mm. With use of the membrane, an experiment for a bulk type optical Kerr shutter device utilizing third-order nonlinear optical effect as shown in FIG. 8 was performed. In FIG. 8, 19 denotes a signal light (wavelength: 0.84 μm) including linearly polarized component, 20 denotes a gate light (wavelength: 0.7 μm) and 21 denotes the membrane made of the organic nonlinear optical material of the present invention (Compound No. 2). 22,22 denote first and second polarizers, 23 denotes a filter for removing the gate light and 24 denotes a photodetector.

When the gate light 20 was not applied to the membrane 21, the signal light 19 did not pass through the second polarizer 22 because the first and second polarizers 22,22 were arranged in a cross-Nicols relationship, so that the light intensity detected with the photodetector 24 was zero. However, when the gate light 20 was applied to the membrane 21, the refractive index of the membrane 21 was changed due to the third-order nonlinear optical effect. As a result, the signal light 19 which had been linearly polarized light became elliptically polarized light, which was able to pass through the second polarizer 22 and detected with the photodetector 24. Thus, an optical Kerr shutter operation was confirmed. The switching speed was in order of not more than nanosecond and a high-speed responsiveness was thus confirmed. The transmission loss of the membrane 21 was not more than 0.1 dB/cm.

EXAMPLE 30

Figure 9:
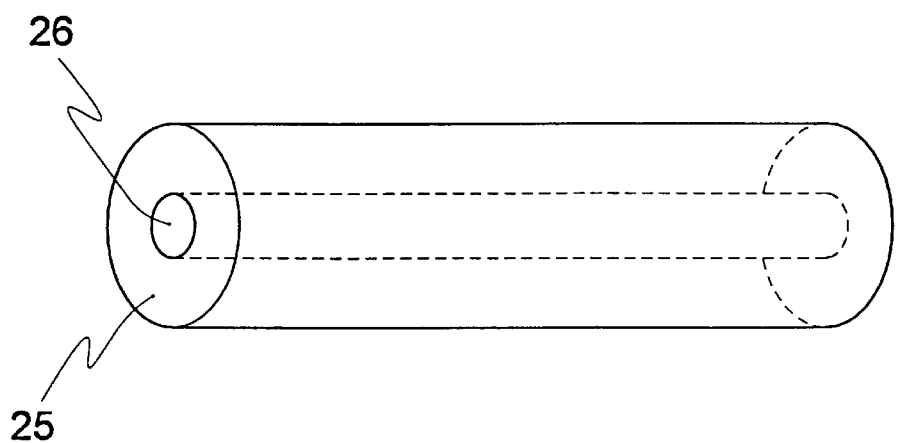
FIG. 9 is a schematic view showing the structure of an optical fiber type optical Kerr shutter element according to the present invention.

The compound described in Example 2 (Compound No. 2) was synthesized in a glass capillary, yielding an optical fiber of the shape as shown in FIG. 9. In FIG. 9, 25 denotes the glass capillary (clad) and 26 denotes a core made of the organic nonlinear optical material of the present invention (Compound No. 2). The diameter of the core was 125 μm and the length of the fiber was 10 cm.

With use of the optical fiber, the same experiment as in Example 29 for an optical Kerr shutter device was performed. As a result, the signal light intensity obtained with use of the optical fiber type optical Keer shutter element was about 20 times that obtained with use of the buk type Kerr shutter element (membrane 21) in Example 29.

As described above, the compound having the iodonium salt structure of the present invention has an advantage that since the compound has large nonlinear optical constants in nonresonant state of a molecule and the compound itself has high light transmittance in visible light region, the compound can be easily made into an organic nonlinear optical material having low loss and high efficacy. For this reason, the compound shows the aforementioned nonlinear optical properties superior to those of the conventional organic nonlinear optical materials and, thus, there can be provided an organic nonlinear optical material which is applicable to electrooptical devices and all optical devices for use in optical communication and optical computer.

What we claim is:

1. An organic nonlinear optical material comprising a compound having the iodonium salt structure represented by the general formula (I):

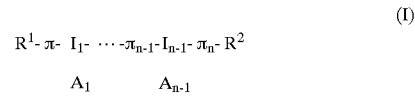

wherein $\pi_1$ to $\pi_n$ are the same or different and each is an atomic group having $\pi$ electron, $I_1$ to $I_{n-1}$ are an iodonium cation, $A_1$ to $A_{n-1}$ are the same or different and each is a counter anion for the iodonium cation, $R^1$ and $R^2$ are the same or different and each is a hydrogen atom or an electron donative group, and n is an integer of 2 to 4, wherein n=2, $\pi_1=\pi_2=$biphenyl ring, $A_1=$trifluoromethanesulfonate ion, $R^1=$H, and $R^2=$methoxy group.

2. An organic nonlinear optical material comprising a compound having the iodonium salt structure represented by the general formula (I):

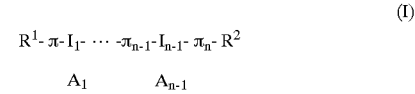

wherein $\pi_1$ to $\pi_n$ are the same or different and each is an atomic group having $\pi$ electron, $I_1$ to $I_{n-1}$ are an iodonium cation, $A_1$ to $A_{n-1}$ are the same or different and each is a counter anion for the iodonium cation, $R^1$ and $R^2$ are the same or different and each is a hydrogen atom or an electron donative group, and n is an integer of 2 to 4, wherein n=3, $\pi_1=\pi_3=$thiophene ring, $\pi_2=$benzene ring, $A_1=A_2=$trifluoromethanesulfonate ion, and $R^1=R^2=$H.

3. A nonlinear optical device of a waveguide structure comprising a light transmitting medium as a waveguide in combination with an optical element, the light transmitting medium comprising a nonlinear optical element comprising an organic nonlinear optical material comprising a compound having the iodonium salt structure represented by the general formula (I):

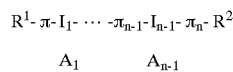

(I)

wherein $\pi_1$ to $\pi_n$ are the same or different and each is an atomic group having $\pi$ electron, $I_1$ to $I_{n-1}$ are an iodonium cation, $A_1$ to $A_{n-1}$ are the same or different and each is a counter anion for the iodonium cation, $R^1$ and $R^2$ are the same or different and each is a hydrogen atom or an electron donative group, and n is an integer of 2 to 4.

4. The nonlinear optical device of claim 3, wherein $\pi_1$ to $\pi_n$ are the same or different and each is an atomic group selected from the group consisting of benzene, biphenyl, thiophene, acetylene, ethynylbenzene, diethynylbenzene, vinylbenzene, naphthalene and anthracene.

5. The nonlinear optical device of claim 3, wherein $R^1$ and $R^2$ are the same or different and each is a member selected from the group consisting of hydrogen atom, alkoxy group, hydroxyl group, amino group, dialkylamino group, alkyl group and trialkylsilyl group.

6. The device of claim 3, which is capable of performing a switching operation by application of a modulated electric field.

7. The device of claim 3, wherein the light transmitting medium has a bulk type structure.

8. The device of claim 3, wherein the light transmitting medium has an optical fiber structure.

* * * * *